US00PP30756P3

(12) United States Plant Patent
Mazzardis

(10) Patent No.: US PP30,756 P3
(45) Date of Patent: Jul. 30, 2019

(54) PLANT NAMED 'NS 13-1'

(50) Latin Name: ***Vaccinium* hybrid**
Varietal Denomination: NS 13-1

(71) Applicant: Vincent David Mazzardis, Joondalup (AU)

(72) Inventor: Vincent David Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 15/732,424

(22) Filed: Nov. 9, 2017

(65) Prior Publication Data

US 2018/0368299 P1 Dec. 20, 2018

(30) Foreign Application Priority Data

Jun. 16, 2017 (QZ) ..... PBR 20171437

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Randall Danskin P.S.

(57) ABSTRACT

A new and distinct variety of blueberry plant, which is denominated varietally as 'NS 13-1' is described, and which produces a fruit having a medium to large fruit size, high fruit sweetness, high fruit firmness, and low fruit acidity and which, when ripe, detaches well from the plant, and which further has a very early fruit production date, when grown under the ecological conditions prevailing near Yanchep Springs, Yanchep, Western Australia.

2 Drawing Sheets

Latin name: '*Vaccinium*' hybrid.
Varietal denomination: 'NS 13-1'.

BACKGROUND OF THE NEW VARIETY

The present invention relates to a new, novel, and distinct variety of blueberry plant '*Vaccinium*' hybrid and which has been denominated varietally as 'NS 13-1'.

ORIGIN AND ASEXUAL REPRODUCTION OF THE NEW VARIETY

The present, new variety of blueberry plant resulted from an ongoing development program of plant breeding. The purpose of this program was to improve the commercial quality of various plant varieties by creating, and releasing, promising selections of plants, including blueberries. To this end, I have made both controlled, and hybrid cross-pollinations each year to produce resulting plant populations from which improved progenies are evaluated and selected.

The blueberry plant 'NS 13-1' was derived from a controlled cross-pollination employing the blueberry plant named 'F1' (unpatented), and which is the seed parent, and blueberry plant 'SCOP18', (unpatented), which is the pollen parent, during the 2011 growing season. This first cross-pollination took place at my property which is located at Yanchep Springs, Yanchep, Western Australia. The seed parent 'F1' is characterized, at least in part, by a spreading growth habit, a very early season flowering date, and further produces large sized, moderately firm fruit. The pollen parent 'SCOP18', on the other hand, is characterized, at least in part, by a semi-upright growth habit, an early ripening date, further produces firm fruit, and the plant produces a very heavy crop load. The seed derived as a result of the first cross-pollination from the seed parent, blueberry plant 'F1', produced approximately 350 plants. These new plants were then grown at my aforementioned property, and the first fruit was evaluated during the 2013 growing season. Further, an additional assessment of these same new plants, which took place in 2013, resulted in the new variety 'NS 13-1' being selected for further asexual reproduction and evaluation. The present, new variety showed desirable traits suitable for a commercial blueberry variety. The present, new variety was asexually reproduced by vegetative cuttings at Yanchep Springs, Yanchep, Western Australia, and the plants produced from this first asexual propagation at Yanchep Springs were again evaluated during the 2013 to 2016 growing seasons. The asexually reproduced plants, which were produced from the aforementioned process, were subsequently evaluated, and were found to be true to the original plant. It was my conclusion, at that time, that the variety 'NS 13-1' was a new, novel, and distinct variety of blueberry plant.

In relative comparison to one of the closest known varieties, that being the 'EB 8-1' blueberry plant (U.S. Plant Pat. No. 25,859) the new variety of blueberry plant is clearly distinguishable. The present, new variety is distinguishable from the 'EB 8-1' blueberry plant (the closest known variety) in view of the fruit it produces, which possesses a high fruit firmness when compared to the fruit produced by the 'EB 8-1' blueberry plant, which produces fruit having a medium fruit firmness. Further, the present, new variety is distinguishable from the 'EB 8-1' blueberry plant (the closest known variety) in view of the fruit is produces, which possesses a high fruit sweetness when compared to the fruit produced by the 'EB 8-1' blueberry plant, which produces fruit having a medium fruit sweetness. Still further, the present, new variety is distinguishable from the 'EB 8-1' blueberry plant in view of the fruit it produces which possesses a low fruit acidity when compared to the fruit produced by the 'EB 8-1' blueberry plant, which produces fruit having a medium fruit acidity. Moreover, the present, new variety is distinguishable from the 'EB 8-1' blueberry plant (the closest known variety) in view of its bush which expresses a low to medium growth vigor when compared to the bush of the 'EB 8-1' blueberry plant, which has a bush expressing medium growth vigor.

The present, new variety is readily distinguishable from its seed and pollen parents. The present, new variety is distinguishable from the seed parent, unpatented blueberry plant 'F1', in view of its bush which expresses a low to medium growth vigor when compared to the bush of the 'F1' blueberry plant, which has a bush expressing medium growth vigor. Further, the present, new variety is distinguishable from the 'F1' blueberry plant (the seed parent) in view of the fruit it produces which possesses a high fruit sweetness when compared to the fruit produced by the 'F1' blueberry plant, which produces fruit having a medium fruit sweetness. Moreover, the present, new variety is distinguishable from the 'F1' blueberry plant in view of the fruit it produces which possesses a high fruit firmness when compared to the fruit produced by the 'F1' blueberry plant, which produces fruit having a medium fruit firmness. Yet further, the present, new variety is distinguishable from the 'F1' blueberry plant (the seed parent) in view of the fruit it produces which possess a low fruit acidity when compared to the fruit produced by the 'F1' blueberry plant, which produces fruit having a medium fruit acidity.

The present, new variety is distinguishable from the pollen parent, unpatented blueberry plant 'SCOP18', in view of its bush which expresses a low to medium growth vigor when compared to the bush of the 'SCOP18' blueberry plant, which has a bush expressing a medium growth vigor. Further, the present, new variety is distinguishable from the 'SCOP18' blueberry plant (the pollen parent) in view of its bush which expresses a spreading growth habit when compared to the bush of the 'SCOP18' blueberry plant, which has a growth habit which is considered semi-upright. Still further, the present, new variety is distinguishable from the 'SCOP18' blueberry plant (the pollen parent) in view of the fruit it produces which possess a high fruit sweetness when compared to the fruit produced by the 'SCOP18' blueberry plant, which produces fruit having a medium fruit sweetness. Additionally, the present, new variety is distinguishable from the 'SCOP18' blueberry plant (the pollen parent) in view of its very early bloom and pick date when compared to the 'SCOP18' blueberry plant, which has an early bloom and pick date.

BRIEF DESCRIPTION OF THE DRAWINGS

The accompanying drawings which are provided are color photographs of the new blueberry plant 'NS 13-1' at four year's age.

Figure 1:
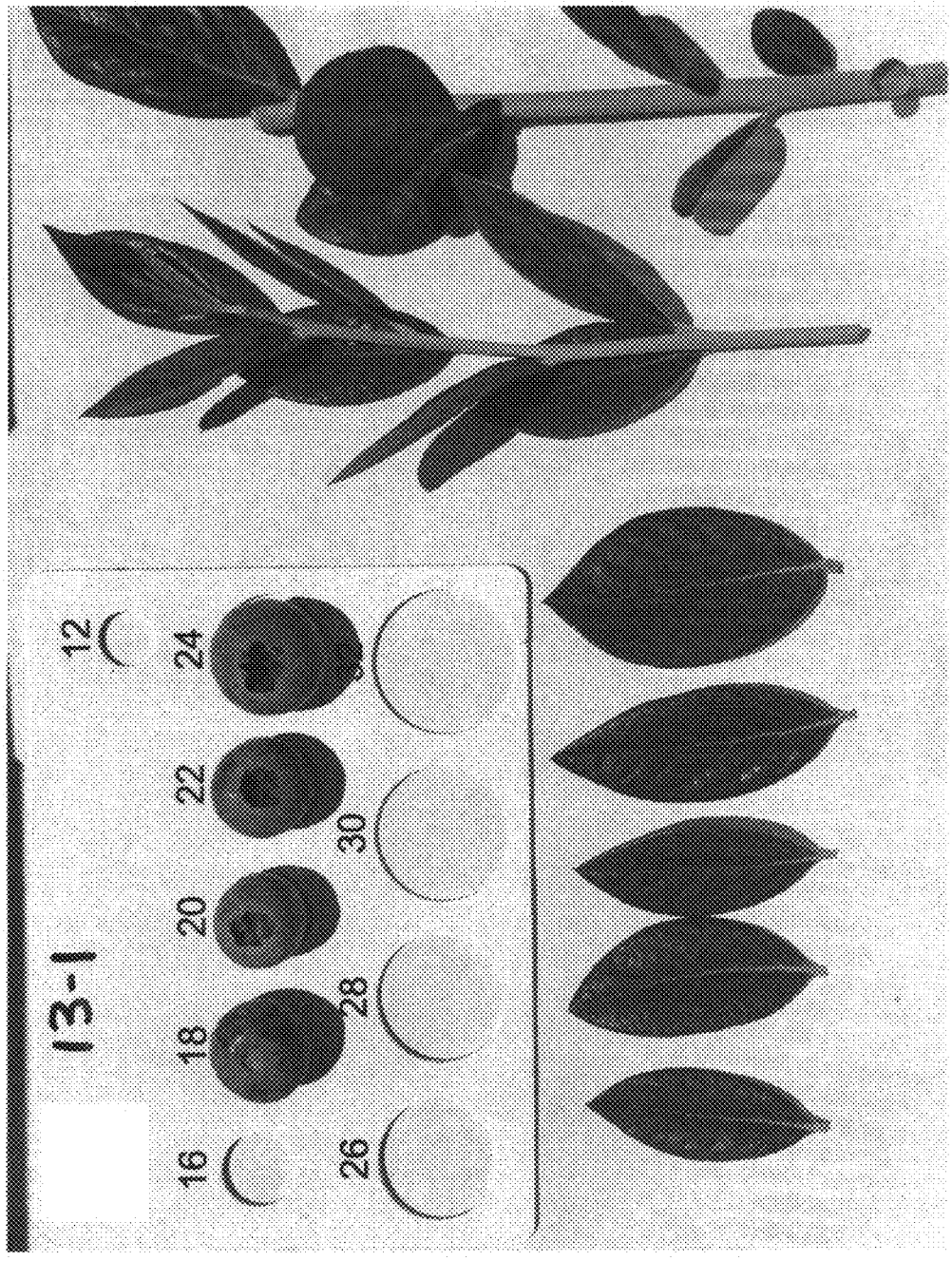
FIG. 1 is a color photograph, which shows the new blueberry plant 'NS 13-1'. This photograph depicts several ripe fruit which are sufficiently mature for harvesting and shipment, and further shows typical shoot-bearing leaves, and several leaves showing the dorsal coloration thereof.
Figure 2:
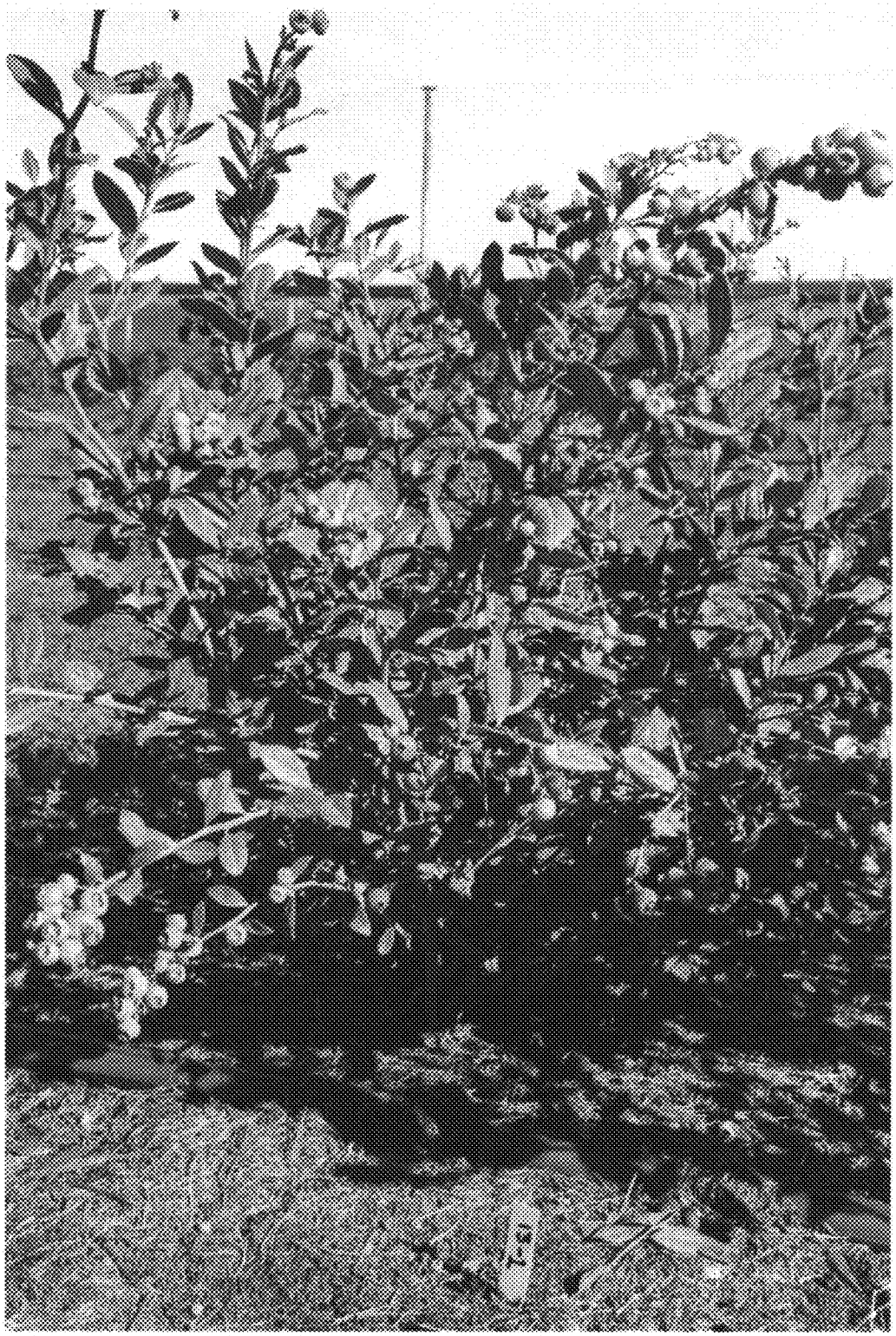
FIG. 2 is a color photograph, which shows the new blueberry plant 'NS 13-1'. This photograph depicts a mature bush with unripe and ripe fruit, the ripe fruit being sufficiently mature for harvesting and shipment, further shows the spreading growth habit of the bush.

The colors in the attached photographs are as nearly true as reasonably possible in a color representation of this type. Due to chemical development, processing and printing, the leaves and fruit depicted in these photographs may or may not be accurate when compared to the actual specimens. For this reason, future color references should be made to the color plates (Royal Horticultural Society Colour Chart $6^{th}$ Edition, hereinafter R.H.S.), and the color descriptions as provided, hereinafter.

NOT A COMMERCIAL WARRANTY

The following detailed description has been prepared solely to comply with the provisions of 35 U.S.C. § 112, and does not constitute a commercial warranty (either expressed or implied), that the present, new variety will, in the future, display the botanical, horticultural, or other characteristics as set forth, hereinafter. Therefore, this disclosure may not be relied upon to support any future legal claims including, but not limited to, breach of warranty and merchantability, or fitness for any particular purpose, or non-infringement which is directed, in whole, or in part, to the present, new variety.

DETAILED DESCRIPTION

Referring more specifically to the botanical details of this new and distinct variety of blueberry plant, the following has been observed during the fifth growing season under the ecological conditions prevailing at the property of the inventor, and which is located near Yanchep Springs, Yanchep, Western Australia.

Plant:

*Plant vigor*.—The present, new variety of blueberry plant is considered to display a low to medium plant vigor.

*Plant growth habit*.—The present, new variety of blueberry plant has a spreading growth habit.

*Size of plant*.—On average, about 1.5 meters by 1.0 meters.

*Internode length*.—One-Year-Old Shoots and Current Season Shoots: About 25.0 millimeters.

*Bark color*.—Grey Orange (RHS 173C).

*Color, one-year-old shoots*.—Yellow Green (RHS 145B).

Leaves:

*Leaf length*.—About 60.0 millimeters. This is considered an average length.

*Leaf width*.—About 32.6 millimeters. This is considered an average width.

*Leaf ratio, length/width*.—On average, about 1.84.

*Color of leaf, dorsal surface*.—Yellow Green (RHS 146A).

*Color of leaf, ventral surface*.—Yellow Green (RHS 147C).

*Color of leaf, vein*.—Yellow Green (RHS 145C).

*Venation pattern of leaf*.—Reticulate.

*Leaf apex texture*.—Glabrous.

*Leaf apex shape*.—Acute.

*Leaf base shape*.—Acute.

*Leaf shape*.—Elliptic.

*Leaf marginal edge*.—Entire.

*Leaf arrangement of plant*.—Alternate.

*Leaf petioles*.—Length. — 2.68 mm. Diameter. — 1.58 mm. Color. — Moderate Yellow Green (RHS 138C).

*Deciduous bud burst, date*.—Not applicable, evergreen.

*Time of vegetative bud burst*.—August-September, under the ecological conditions prevailing near Yanchep Springs, Yanchep, Western Australia.

Flowers:

*Number of flowers*.—About 5-8.

*Inflorescence length, excluding peduncle*.—About 17 millimeters.

*Flower bud coloration*.—The presence of anthocyanin is considered very weak in the flower buds.

*Beginning of flowering on one-year-old shoots*.—Considered very early in the growing season.

*Beginning of flowering on current year's shoots*.—Considered very early in the season.

*First bloom, date*.—January-February under the ecological conditions prevailing near Yanchep Springs, Yanchep, Western Australia.

*Bloom time, duration*.—8 weeks under the ecological conditions prevailing near Yanchep Springs, Yanchep, Western Australia.

*Corolla shape*.—Urceolate.

*Corolla ridges*.—Present.

*Corolla length*.—On average, about 7.8 millimeters.

*Corolla diameter*.—On average, about 10.4 millimeters.

*Corolla aperture size*.—On average, about 6.0 millimeters.

*Corolla tube coloration*.—White (RHS NN155D).

*Pedicel color*.—Green (RHS 142B).

*Pedicel length*.—On average, about 6.3 millimeters.

*Calyx diameter*.—On average, about 6.0 millimeters.

*Calyx basin depth*.—On average, about 2.0 millimeters.

*Attitude of sepals*.—Considered to be erect.

*Type of sepals*.—Straight.

Reproductive organs:

*Pollen anthers, size*.—On average, about 4.4 millimeters.

*Pollen anthers, color*.—Grey Orange (RHS 167C).

*Pistil, length*.—On average, about 8.85 millimeters.

*Pistil, color*.—Yellow Green (RHS 145B).

*Pollination requirements*.—The variety is self-fertile.

Fruit:

*Unripe fruit, color*.—Yellow Green (RHS N144D).

*Unripe fruit, intensity of green color*.—Considered low for the species.

*Ripe fruit skin, color*.—Bluish Black (RHS 203C).

*Ripe fruit flesh, color*.—Yellow Green (RHS 145C).

*Seeds, color*.—Grey Orange (RHS 167D).

*Fruit size*.—On average, about 20.0 mm in diameter with height 15.3 mm.

*Fruit weight*.—On average, about 4.0 grams.

*Fruit production*.—On two-year-old bush, on average, 4 kilograms.

*Berry shape*.—Oblate.

*Sweetness, when ripe*.—Considered high.

*Firmness, when ripe*.—Firm.

*Acidity, when ripe*.—Low for the species.

*Cluster density*.—Medium.

*Storability of the fruit*.—Considered Excellent.

*Market use*.—First Grade Fresh Market Fruit.

*First pick date*.—April under the ecological conditions prevailing near Yanchep Springs, Yanchep, Western Australia.

*Lack pick date*.—June under the ecological conditions prevailing near Yanchep Springs, Yanchep, Western Australia.

*Plant fruiting type*.—Generally speaking, fruiting occurs on one-year-old, and current season's shoots.

*Beginning of fruit ripening on one-year-old shoots*.—Considered to be very early in the season.

*Beginning of fruit ripening on current year's shoots*.—Considered to be very early in the season.

*Resistance to insects and diseases*.—No particular susceptibilities were noted. The present, new variety has not been tested to expose or detect any susceptibilities or resistance to any known plant and/or fruit diseases.

Although the new variety of blueberry plant possesses the described characteristics when grown under the ecological conditions prevailing near Yanchep Springs, Yanchep, Western Australia, it should be understood that the variations of the usual magnitude and characteristics incident to changes in growing conditions, fertilization, pruning, pest control, frost, climatic variables and horticultural management are to be expected.

Having thus described and illustrated my new variety of blueberry plant, what I claim is new, and desire to secure by plant Letters Patent is:

1. A new and distinct variety of blueberry plant, substantially as illustrated and described, and which is characterized principally as to novelty by producing a fruit having a medium to large fruit size, high fruit sweetness, high fruit firmness, and low fruit acidity and which, when ripe, detaches well from the plant, and which further has a very early fruit production date, when grown under the ecological conditions prevailing near Yanchep Springs, Yanchep, Western Australia.

* * * * *